US006677604B2

(12) United States Patent
Mitrovic

(10) Patent No.: US 6,677,604 B2
(45) Date of Patent: Jan. 13, 2004

(54) OPTICAL SYSTEM AND METHOD FOR PLASMA OPTICAL EMISSION ANALYSIS

(75) Inventor: Andrej Mitrovic, Phoenix, AZ (US)

(73) Assignee: Tokyo Electron Limited, Tokyo (JP)

( * ) Notice: Subject to any disclaimer, the term of this patent is extended or adjusted under 35 U.S.C. 154(b) by 0 days.

(21) Appl. No.: 10/096,932

(22) Filed: Mar. 14, 2002

(65) Prior Publication Data

US 2002/0139925 A1 Oct. 3, 2002

Related U.S. Application Data

(60) Provisional application No. 60/279,722, filed on Mar. 30, 2001.

(51) Int. Cl.[7] .................... G01N 15/06; G01N 21/49; G01N 21/85
(52) U.S. Cl. .................... 250/573; 250/226; 356/316; 356/419
(58) Field of Search ............... 250/208.2, 226, 250/216, 234, 214 R, 559.01, 554, 227.18, 339.15, 573, 564, 343, 345; 356/338, 432, 315–316, 417, 419

(56) References Cited

U.S. PATENT DOCUMENTS

| | | | | |
|---|---|---|---|---|
| 4,326,802 A | * | 4/1982 | Smith et al. | 356/316 |
| 4,707,147 A | * | 11/1987 | Aoki et al. | 374/161 |
| 5,515,169 A | * | 5/1996 | Cargill et al. | 356/417 |
| 5,889,587 A | * | 3/1999 | D'Silva et al. | 356/316 |
| 5,986,277 A | * | 11/1999 | Bourque et al. | 250/554 |
| 5,995,235 A | * | 11/1999 | Sui et al. | 356/419 |
| 6,366,346 B1 | * | 4/2002 | Nowak et al. | 356/72 |

* cited by examiner

Primary Examiner—David Porta
Assistant Examiner—Patrick J. Lee
(74) Attorney, Agent, or Firm—Oblon, Spivak, McClelland, Maier & Neustadt, P.C.

(57) ABSTRACT

An apparatus (10) and method for detecting and analyzing the spectra of light emitted by a plasma (36) in a plasma duct (16) having a plurality of windows (40) formed therein. In one embodiment, the apparatus includes an optical system (50) arranged adjacent each window that directs light emanating from the plasma and passing through each window to two or more optical filters (F1, F2) having different bandwidths so that different portions of the light spectra (S1, S2) can be measured. The filter light is incident respective two or more detectors (D1, D2), which produce an electrical signal representative of the intensity of light incident thereon, and thus is a measure of the content of a select band of the light spectrum. Performing this measurement for different regions (R) of the plasma yields different spectra and thus provides information about the plasma properties, thereby allowing for adjustment of those properties. The adjustment can be made by selectively providing electrical power to electrodes (E) formed in the plasma duct and in operable communication with the plasma. Other embodiments of the apparatus are disclosed that involve a translatable optical system and fiber optical systems. Methods for measuring the emitted spectra and adjusting the plasma properties in response thereto are also disclosed.

38 Claims, 9 Drawing Sheets

OPTICAL SYSTEM AND METHOD FOR PLASMA OPTICAL EMISSION ANALYSIS

CROSS-REFERENCE TO RELATED APPLICATION

This application claims priority to U.S. Application Ser. No. 60/279,722, filed Mar. 30, 2001. The contents of that application are incorporated herein by reference.

BACKGROUND OF THE INVENTION

1. Field of the Invention

The present invention relates to plasma processes, and in particular to optical systems and methods for detecting and analyzing optical emissions from the plasma along the length of the plasma.

2. Discussion of the Background

Plasma is used in various types of industrial processes, such as semiconductor manufacturing (e.g., integrated circuit fabrication and printed wiring board interconnections), medical equipment manufacturing and automobile manufacturing. One common use of plasma is for etching away materials in an isolated or controlled environment. One or more plasma compositions may etch various types of materials, including glasses, silicon or other substrate materials, organics such as photoresist, waxes, plastics, rubbers, biological agents, and vegetable matter, and metals such as copper, aluminum, titanium, tungsten, and gold. Plasma is also utilized for depositing materials, such as organics and metals, onto an appropriate surface by various techniques, such as via chemical vapor deposition. Sputtering operations may also utilize a plasma to generate ions that sputter away material from a source (e.g., metals, organics) and deposit those materials onto a target. Surface modification operations also use plasmas, such as surface cleaning, surface activation, surface passivation, surface roughening, surface smoothing, micromachining, hardening, and patterning.

Creating a plasma for manufacturing processes is typically done by introducing a low-pressure process gas into a plasma duct surrounding a work piece (substrate), such as an integrated circuit (IC) wafer. The molecules of the low-pressure gas in the chamber are ionized by a radio frequency (RF) power source to form a plasma that flows over the substrate. The plasma duct is used to maintain the low pressure required for the plasma and to serve as a structure for attaching one or more electrodes that couple electrical power to the plasma.

Plasma may be created from a low-pressure process gas by inducing an electron flow that ionizes individual gas molecules by transferring kinetic energy through individual electron-gas molecule collisions. Typically, electrons are accelerated in an electric field such as one produced by RF power. This RF power may have a low frequency (below 550 KHz), high frequency (13.56 MHz), or a microwave frequency (2.45 GHz).

Etching may be performed by plasma etching or reactive ion etching (RIE). A plasma etching system may include a single RF power source, or a plurality of such sources operating at one or more frequencies with a corresponding number of electrodes, at least one of which is located within the process chamber. A plasma is generated adjacent the substrate, the latter typically being co-planar with the electrode and supported by a substrate support member within the process chamber. The RF energy may be coupled to the plasma by capacitive means, by inductive means, or by both capacitive and inductive means. The chemical species in the plasma are determined by the source gas(es) used.

A plasma may also be used in chemical vapor deposition (CVD) to form thin films of metals, semiconductors or insulators (or, conducting, semiconducting or insulating materials) on a semiconductor wafer. Plasma-enhanced CVD uses the plasma to supply the required reaction energy for depositing the desired materials. Typically, RF energy is used to produce this plasma.

Unfortunately, it is difficult to quickly assess the quality of the etching or deposition process in plasma processing. Presently, one of the main methods used to assess processing quality for a given plasma process involves the steps of processing a wafer in the reactor, removing the wafer, and then examining the wafer. (Those steps may be tedious and costly.) Furthermore, changes in the process due to equipment malfunctions, such as defects in mass flow controllers, almost always reduce process yields, and cannot generally be corrected until after test wafers have been processed and examined, which is a timely and expensive proposition.

Optical emission spectroscopy is a method currently used to detect a process endpoint in plasma etching systems. U.S. Pat. Nos. 5,658,423, 6,090,302 and 5,347,460 disclose different optical emission spectroscopy methods. Optical emission spectroscopy is performed in situ and is possible because the plasma excites certain atomic and molecular species present in the plasma and causes them to emit light of wavelengths that are characteristic of the species present in the etch chemistry. Plasma properties, including ion/electron density, electron temperature and relative chemical species concentrations, can be deduced from collecting and analyzing the optical emissions from the plasma.

In an optical monitoring system for performing optical emission spectroscopy, specific wavelengths of the light emitted from the plasma are selected and fed to detectors, such as photodiodes, photomultipliers, and array detectors, which convert the light intensities into electrical signals. It is known that the intensity of the detected raw signals is related to the concentration of excited species. By selecting wavelengths that correlate to the reaction products of the particular process, the process may be monitored either at specific wavelengths or at all wavelengths by a spectral scan.

In a particular application, end-point detection of a plasma process of a substrate having multiple layers may be performed by selecting a wavelength corresponding to the emissions generated by a layer below the layer being etched. When the layer being etched has been completely removed from the underlying layer, the chemical composition of both the gas phase and the remaining layer changes. Product species from the etched layer are no longer generated, and the concentration of some reactants increases because they are no longer being consumed by the reaction. These chemical changes show up as changes in optical emission intensities of the plasma.

BRIEF SUMMARY OF THE INVENTION

Recognizing that plasma properties can vary over the length of the plasma, particularly along the axial direction of the duct in which the plasma is formed, the present invention relates to plasma processes, including optical systems and methods for detecting and analyzing optical emissions from the plasma along the length of the plasma.

According to a first aspect of the present invention, an apparatus detects and analyzes the spectra of light emitted by a plasma at multiple locations along the plasma as contained in a plasma duct. One such plasma duct has an outer wall with a plurality of locations (either in the same or different windows) transparent to the optical emissions. Such an apparatus may include a plurality of optical systems (e.g., adjacent the one or more windows), each capable of redirecting light entering therein. A beam splitter is arranged relative to the optical systems so as to receive light from the optical systems and direct the light along first and second optical paths. A first optical filter having a first bandwidth is arranged in the first optical path, and a second optical filter having a second bandwidth is arranged in the second optical path. First and second detectors are respectively arranged downstream of the first and second optical filters so as to detect light passing through the respective filters and convert the light into respective first and second electrical signals. Those electrical signals are representative of the intensity of light incident the first and second detectors.

In an alternate embodiment, instead of having a plurality of optical systems, a single optical system is arranged so as to be (1) translatable along the plasma duct and (2) in optical communication with the plasma through plural locations in the plasma duct (either in the same or different windows). The optical system may include an optical fiber that couples a collection optical system ("collection optics") arranged adjacent the plasma duct and a receiving optical system ("receiving optics") at the end of the optical fiber opposite the collection optics.

According a second aspect of the present invention, the spectral properties of light emitted by a plasma at different regions of the plasma are measured. One possible environment is the apparatus of the first aspect, although the method can be used in any apparatus that supports measurements at multiple locations. The method sequentially collects light generated by the plasma in different areas. The sequentially collected light is separated into at least two paths and the sequentially collected light in each path is passed through a respective optical filter. Each optical filter has a different spectral bandwidth than the other filters so that each component of the spectrum can be isolated and measured. The filtered light is then detected from each path using corresponding detectors. Each detector can then generate a corresponding electrical signal representative of the intensity of the light detected.

In one embodiment of that method, the step of sequentially collecting light is performed by providing at least one optical system adjacent the plasma duct and shuttering all but one optical system at a time so that the optical emissions from different regions of the plasma can be analyzed.

In another embodiment of that method, the plasma properties are adjusted by selectively activating one or more electrodes based on the information contained in the electrical signals from the detectors.

DETAILED DESCRIPTION OF THE PREFERRED EMBODIMENTS

The present invention relates to plasma processes, and in particular to optical systems and methods for detecting and analyzing optical emissions from the plasma along the length of the plasma. In the Figures, like reference numbers are used to indicate like elements throughout.

Figure 1:
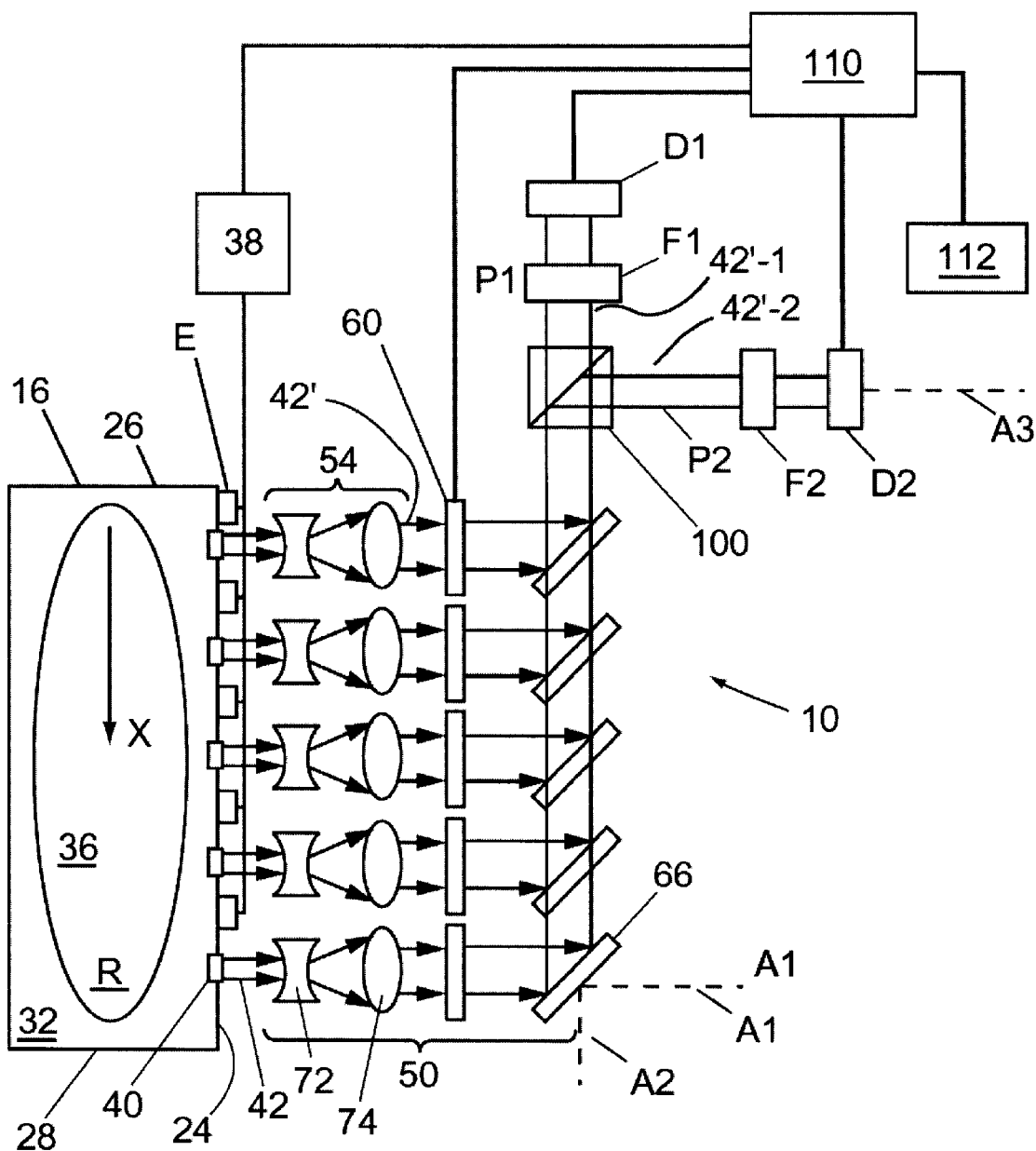
FIG. 1 is a schematic cross-sectional diagram of the optical spectroscopy apparatus of the present invention in combination with a plasma duct.

With reference to FIG. 1, there is shown indexing optical spectroscopy apparatus 10 in combination with a plasma duct 16 having an outer wall 24, an upper opening 26 and a lower opening 28 enclosing an interior region 32 capable of containing a plasma 36. Different regions of the plasma are indicated as R. Outer wall 24 includes a plurality of windows 40 transparent to light 42 (shown as beam) emitted from plasma 36 and resistant to etching by the plasma. An exemplary window 40 is made of quartz or fused silica. Duct 16 also preferably includes a plurality of electrodes E formed in outer wall 24 in between windows 40 and in operative communication with interior region 32. Electrodes E may be DC electrodes, RF electrodes or inductive coils, and serve to form plasma 36 in interior region 32. Electrodes E are electrically connected to an electrical power source 38 capable of providing the appropriate electrical power (e.g., DC or RF) to each of the electrodes. Electrical power source 38 may include, for example, an array of RF power sources, with each power source electrically connected to a corresponding electrode E.

Arranged adjacent windows 40 is an optical system 50 that includes, along an optical axis A1, collection optics 54, a shutter 60 and a fold mirror 66. Collection optics 54 is arranged to collect light 42 passing through window 40 and relay the light to shutter 60. In a first embodiment, collection optics 54 includes optical elements (e.g., lenses 72 and 74) arranged as a beam expander. Lenses 72 and 74 may be movable to adjust the size of light beam 42' incident shutter 60. An exemplary configuration of collection optics 54 is an adjustable (e.g., zoom) Galilean or inverse Galilean telescope. Shutter 60 is preferably electronically operated.

Fold mirrors 66 are preferably beam-splitting mirrors that allow light incident thereon from one direction to pass therethrough while also reflecting a portion of light incident thereon from another direction (e.g., at right angles to the first direction, as shown). Note that the fold mirror 66 associated with the optical system 50 nearest lower opening 28 can be entirely reflecting. Mirrors 66 are arranged along a common axis A2, which is at right angles to axis A1.

System 10 further includes a beam splitter 100 arranged along axis A2 downstream from mirrors 66 that splits the optical path into two paths; a first path P1 that continues along axis A2, and another path P2 along an axis A3 at right angles to axis A2. Arranged along axis A2 downstream of beam splitter 100 is a first optical filter F1 having a first spectral bandwidth. A first detector D1 is arranged along axis A2 downstream of first filter F1. Arranged along axis A3 is a second optical filter F2 having a second spectral bandwidth. A second detector D2 is arranged along axis A3 downstream of first filter F2. In general, N such filters and detectors can be so arranged. Detectors D1 and D2 are selected to detect light passing through filters F1 and F2, respectively. Exemplary detectors D1 and D2 include photomultiplier tubes or photodiodes.

Filters F1 and F2 are interchangeable with other filters having a different bandwidth. The spectral bandwidth of filters F1 and F2 are selected to correspond to wavelengths associated with the optical emission spectrum of plasma 36. For instance, in a fluorocarbon etch chemistry, one might be interested in the relative ratio of the fluorine population to the argon population. Thus, the emission intensity at 703 nm for the light associated with the decay of electron-induced excitation of fluorine F* and the emission intensity at 750 nm for the light associated with the decay of electron-induced excitation of argon Ar* is monitored. Accordingly, filters F1 and F2 having a small wavelength bandwidth about 703 nm and 750 nm, respectively, are selected. Assuming similar electron cross-sections, the ratio of the two emission intensities is proportional to the ratio of the excited specie concentrations (i.e. F*/Ar*), which is, in turn, proportional to the ratio of each specie (i.e. F/Ar). This example is further discussed in the article entitled "Optical diagnostic techniques for plasma processing," by Gary S. Selwyn, AVS Monograph Series, M-11, AVS Press, 1993.

Additionally, the filters F1 and F2 may be selected to pass plasma light emission corresponding to two different Ar emission lines, $Ar^*_1$ and $Ar^*_2$. It is well known in the literature that the ratio of the emission intensities $I_{\lambda 1}/I_{\lambda 2}$ is inversely proportional to the wavelength ratio and a function of the electron temperature $T_e$ for a Maxwellian electron energy distribution function, viz. $I_{\lambda 1}/I_{\lambda 2} \propto (\lambda_2/\lambda_1) f(T_e)$. Moreover, one may also empirically determine a relationship between Ar emission intensity at a specific wavelength and plasma density measured using an alternative device such as a Langmuir probe. Thereafter, one may measure the Ar emission intensity and estimate the local plasma density via a "look-up" table assembled from measurements performed at an earlier time in the current plasma duct configuration.

With continuing reference to FIG. 1, electrically connected to detectors D1 and D2 is an electronic controller 110 capable of receiving and processing electrical signals from detectors D1 and D2. Controller 110 also is electrically connected to electrical power source 38 and is capable of controlling the power source to provide select amounts of power to each of electrodes E. Controller 110 is also electronically connected to shutters 60 to control and coordinate their operation, as explained below. Controller 110 preferably includes an interface 112 for inputting information into the controller and displaying information from the controller. An exemplary controller 110 is a computer having a memory unit and a processor, such as a PENTIUM™ processor, as well as data acquisition and control capability. Interface 112 may include a standard computer keyboard, a mouse and a display monitor. A suitable computer for controller 110 is a DELL PRECISION WORKSTATION 610™, available from Dell Corporation, Dallas, Tex.

Method of Operation

Figure 2:
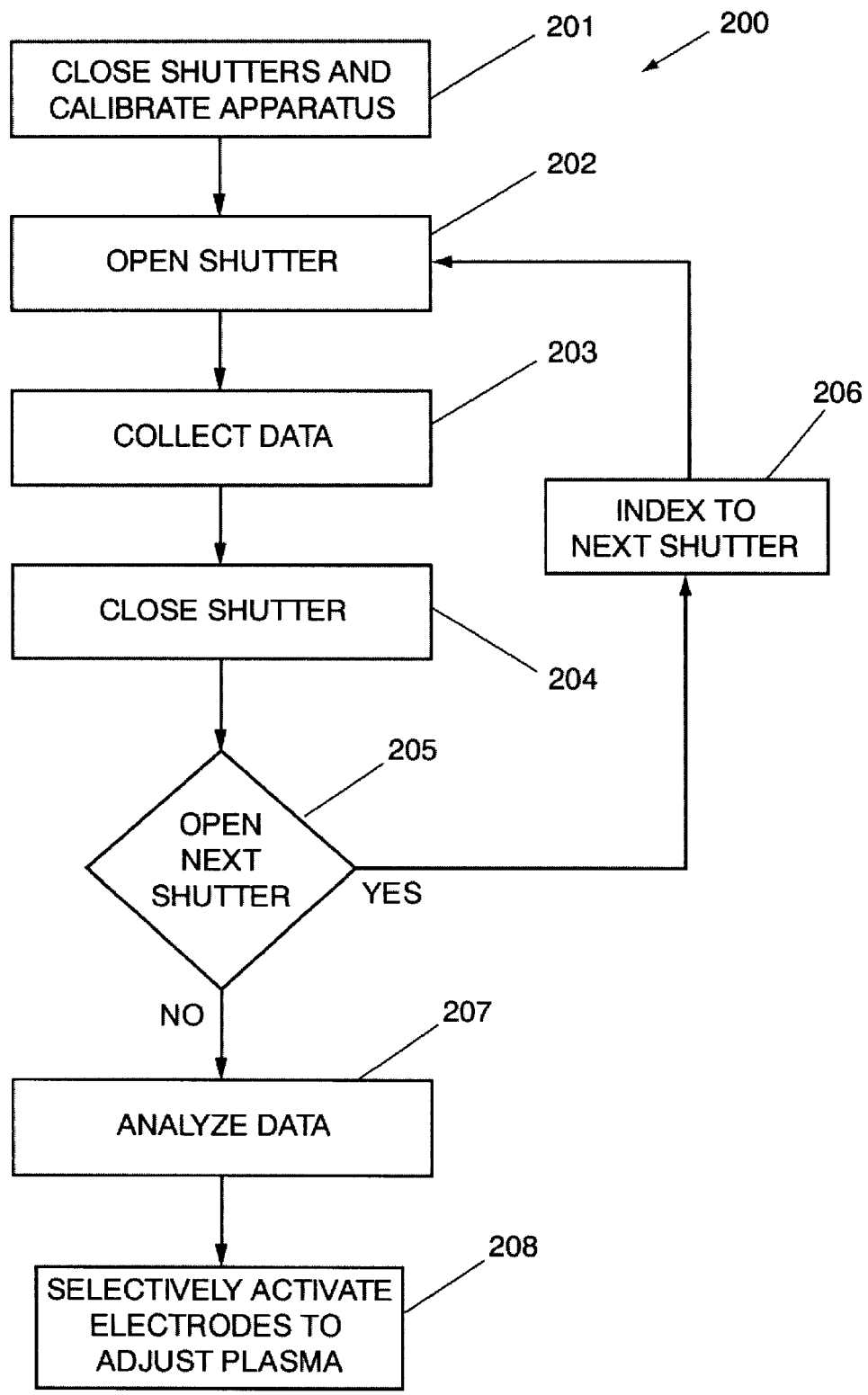
FIG. 2 is a flow diagram of the steps of operating the apparatus of FIG. 1 to measure and analyze the optical emissions from the plasma.

With continuing reference to FIG. 1 and also with reference now to FIG. 2 and flow diagram 200 therein, the method of operation of apparatus 10 is now described. The method steps below presume that plasma 36 is already formed within plasma duct 16.

In step 201, controller 110 sends an electronic signal to shutters 60 that closes the shutters to ensure that light 42 emanating from plasma 36 is blocked so that the background noise from detectors D1 and D2 can be measured and the apparatus calibrated. The calibration is discussed in greater detail below.

After the apparatus is calibrated, then in step 202, controller 110 sends an electronic signal to shutters 60 that opens a shutter in a select optical system 50. For example, to measure the properties of plasma 36 closest to upper opening 26, shutter 60 associated with the optical system 50 closest to the upper opening is opened. Light 42 passing through optical system 50 and is formed into beam 42', which passes through opened shutter 60 and is incident the associated fold mirror 66. With the exception of the optical system closest to upper opening 26, the light reflected from associated fold mirror 66 passes through at least one of the other fold mirrors and is incident beam splitter 100. The latter divides the light into two beams, 42'-1 and 42'-2 that travel along optical paths P1 and P2, respectively.

Figure 3A:
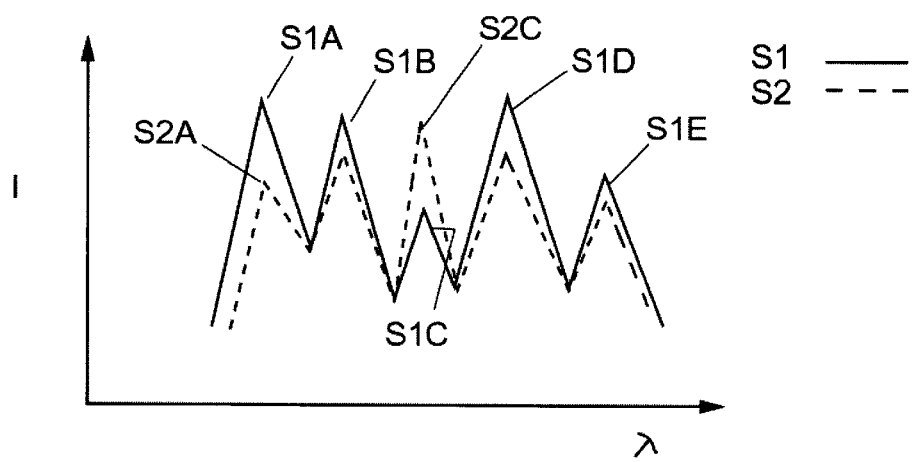
FIG. 3A is a plot of the intensity (I) versus the wavelength ( ) of example emission spectra, represented by solid and dashed lines, of light emitted by two different regions of the plasma prior to passing through the bandwidth filters.
Figure 3B:
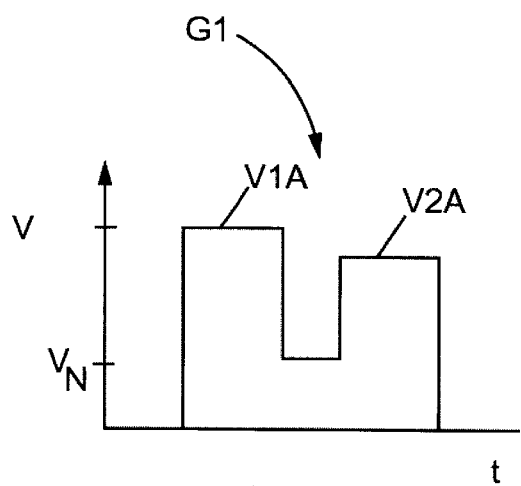
FIGS. 3B AND 3C present plots of the voltage (V) versus time (t) as detected by the detectors associated with the respective bandwidth filters for light emitted from two different regions of the plasma for the two different spectra.

Next, in step 203, data corresponding to the spectral signature of the light emitted from plasma 36 in the region R being measured is collected. With reference now to FIGS. 3A and 3B, light beams 42'-1 and 42'-2 incident respective filters F1 and F2 each have the same spectrum S1 (FIG. 3A). Light beam 42'-1 is incident filter F1, which allows only a select portion (e.g., peak S1a) of the spectral bandwidth to pass therethrough and be incident detector D1. Similarly, beam 42'-2 is incident filter F2, which allows only a select portion (e.g., peak S1c) of the spectral bandwidth to pass therethrough and be incident detector D2. With reference now to FIG. 3B and graph G1, detectors D1 and D2 output respective voltages V1a and V1b corresponding to the intensity I of the light incident thereon. In the plots of V vs. time (t), $V_N$ is the noise voltage present when no light is incident the detectors.

Next, in step 204, controller 110 sends an electronic signal to shutters 60 to close the open shutter. Then, in step 205, controller 110 inquires whether the next shutter should be opened or if the process should continue to the data analysis step. Controller 110 may be pre-programmed, for instance, to cycle through all the shutters in a particular order. Alternatively, if another shutter is to be opened, then in step 206, the process indexes to the next shutter, and step 202 of opening the shutter and step 203 of collecting data are repeated. Steps 202–205 provide for sequentially collecting light generated by different regions R of the plasma.

Figure 3C:
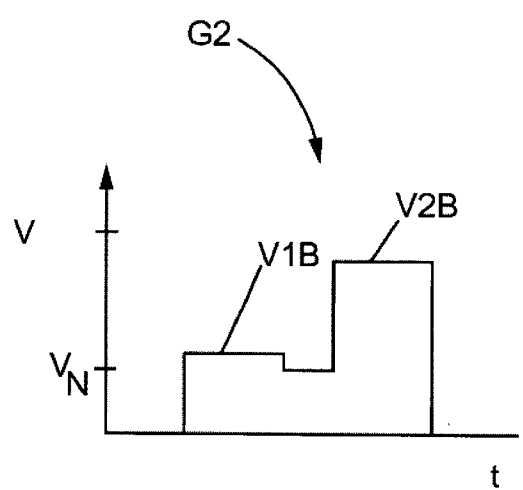

With reference now to FIG. 3C, there is shown in graph G2 second voltage signals V1b and V2b associated with the detected intensity of filtered spectra S2a and S2c from a second spectrum S2 (see FIG. 3A). Spectrum S2, which is taken from a different region R of plasma 36, has a peak S2a with a lower intensity than corresponding peak S1a of spectrum S1, and a peak S2b with a higher intensity than corresponding peak S1b of spectrum S1. This is reflected in the output voltages V1b and V2b from detectors D1 and D2, respectively.

Once all of the shutters have been cycled through according to the programmed instructions provided to controller 110, then the method proceeds to step 207, where the data is analyzed. This analysis includes recording analog voltages output from detectors D1 and D2 (see FIG. 1) digitally within control electronics processor 110 through A/D interface, and calibrating the resultant voltage traces. Following the description provided above, the ratio of voltages recorded at separate wavelengths is equivalent to the ratio of emission light intensities once the voltage ratio is corrected for the quantum efficiency wavelength dependence of the photo-detector. For example, most photo-multiplier tubes exhibit a wavelength dependence for photo-cathode radiant sensitivity or quantum efficiency; however, it is usually designed to be fairly "flat" across a prescribed spectral range. Once a PMT is selected for the given application, it is accompanied by a quantum efficiency-wavelength calibration performed by the manufacturer. Using this calibration curve, the recorded voltage ratio (above) is corrected by the ratio of quantum efficiencies at the two wavelengths and then the calibrated voltage ratio is equivalent to the intensity ratio, which is, in turn, equivalent to the specie concentration ratio as described above. Following this procedure, specie concentration ratios may be computed at each spatial location along the length of the plasma duct 16 and subsequently monitored in time.

Following the above method, the spectral content of plasma 36 can be obtained for multiple bandwidths for different plasma regions R by using a desired number of filters and detectors. Also, the spectral content of plasma 36 can be obtained at times t, $t+\Delta t_{scan}, \ldots, t+m\Delta t_{scan}$, where $\Delta t_{scan}$ is the time increment for each site measurement and m is the number of measurement sites corresponding to the location of optical systems 50. A scan of the spectral content of plasma 36 using the plurality of optical assemblies 50 may be performed in time increments of $\Delta t_{sample} \geq m\Delta t_{scan}$.

Filter Wheel Embodiment

Figure 4:
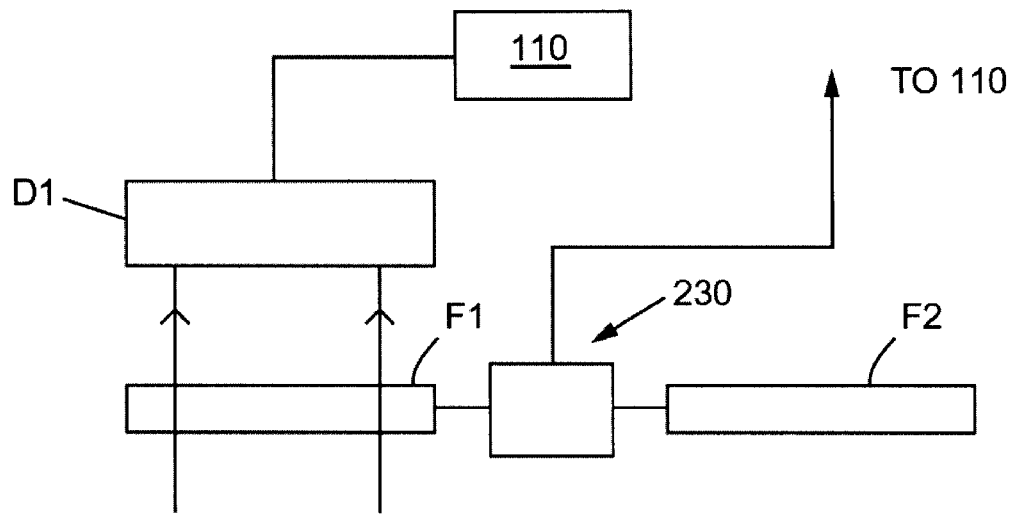
FIG. 4 is a schematic diagram of a first alternate embodiment of the apparatus of FIG. 1, wherein the filters are arranged on a multiple-filter device and used in combination with a single detector and a single optical path.

With reference to FIG. 4, in a first alternate embodiment to apparatus 10, a single detector and a multiple-filter device 230, such as a filter wheel, can be used to simplify the apparatus by eliminating the need for multiple detectors and beam splitter 100. Device 230 includes multiple filters F1, F2, ... Fn (only F1 and F2 are shown for simplicity) and is preferably electronically connected to and controlled by controller 110. Controller 110 is programmed to correlate the particular filter (F1, F2, ... Fn) placed in optical path P1 with the appropriate voltage measurements from detector D1 to create and store essentially the same voltage (V) vs. time (t) record as is shown in FIG. 3B or 3C.

Translatable Optical System

Figure 5:
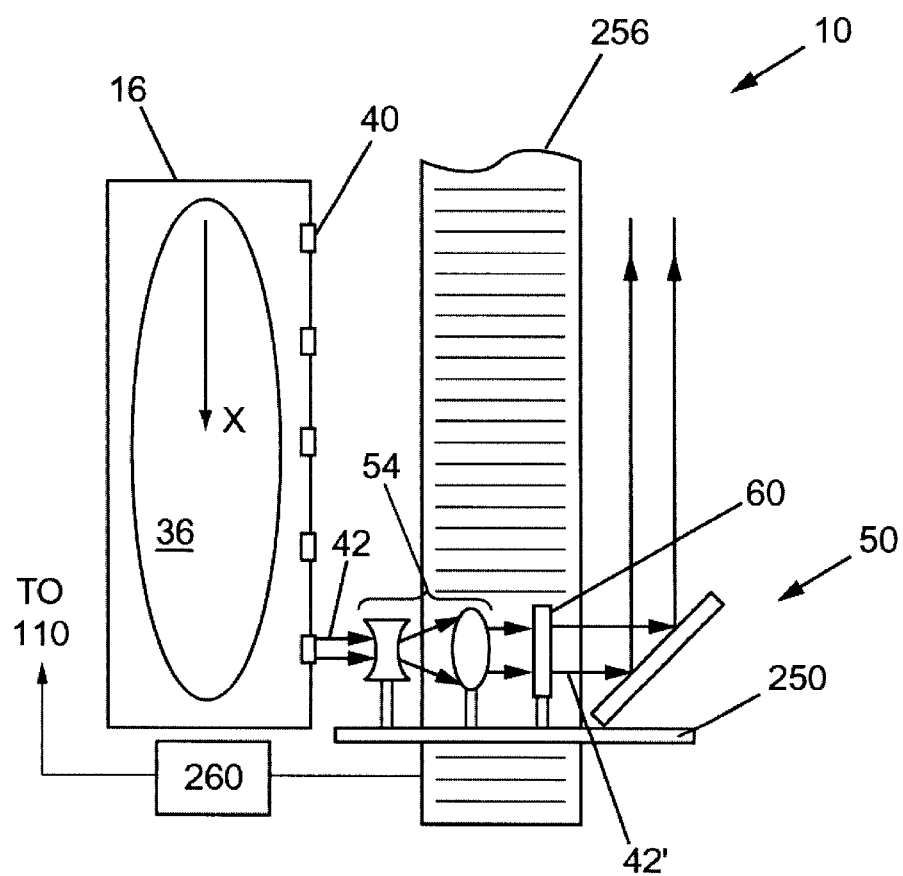
FIG. 5 is a schematic diagram of a second alternate embodiment of the apparatus of FIG. 1 that employs a single optical apparatus arranged on a translatable optics mount.

With reference now to FIG. 5, in a second alternate embodiment, apparatus 10 includes a single optical system 50 mounted to an optics mount 250 (e.g., a stage or lens barrel) that is translatable (e.g., in the x-direction and/or the y-direction) along outer wall 24 of plasma duct 16 (e.g., by means of a linear track 256, a planar mount (not shown) or a two- or three-dimensional robot arm (not shown)) to which the optics mount is mechanically engaged. In the linear track embodiment, a linear motor 260 is operatively connected to linear track 256 to control the movement of mount 250 so that optical system 50 is in optical communication with a particular location. Motor 260 is electronically connected to controller 110, which controls the movement of mount 250 and thus the coordinated positioning of optical system 50 to obtain spectral emission data along various locations in the plasma 36.

Figure 6:
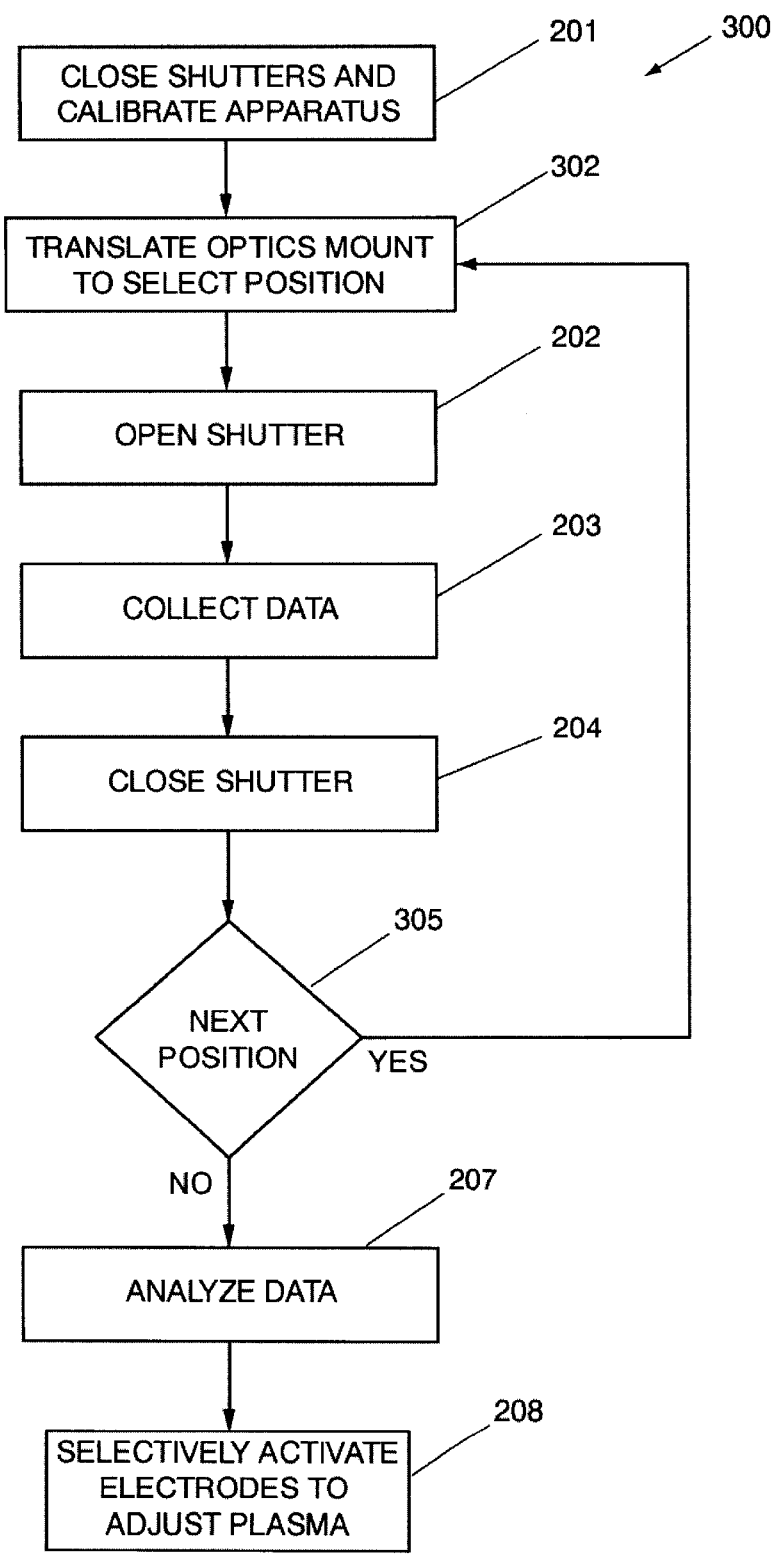
FIG. 6 is a flow diagram of the method steps of operating the apparatus of FIG. 5 to measure and analyze the optical emissions from the plasma.

The method of operation of apparatus 10 of this second alternate embodiment is described in flow diagram 300 of FIG. 6. The method steps are essentially the same as that in flow diagram 200 of FIG. 2, except that a step 302 is inserted between steps 201 and 202. Step 302 involves controller 110 sending an electrical signal to an actuator (e.g., linear motor 260 or robot arm motors), which translates the optics mount to a selected position according to instructions programmed into the controller. Also, after step 204, a new step 305 inquires whether mount 250 should be moved to a "next position." If so, then the method returns to step 302 where optics mount 250 is translated to the next position and steps 202–204 repeated.

In an alternate embodiment, plural optical systems are mounted on the optics mount 250 simultaneously to reduce the distance that the mount must move and to increase parallel processing. For example, in a six-position system with two optical systems on the same optics mount, the first optical system can receive light passed from a first position while a second optical system receives light passed from a fourth position. (The light can be received either truly simultaneously, or one after another using shutters 60, as described above.) The mount can then be moved such that the first and second optical systems receive light through the second and fifth positions, respectively. Later, the mount can then be moved again such that the first and second optical systems receive light through the third and sixth positions, respectively.

Conversely, plural mounts can be used to overlap movement of one optics mount 250 with measurements by an optics system on another optics mount 250. For example, using the six-position example above, after the first optics system has finished measuring at the first location, it may begin moving to the second location while the second optics system begins measuring at the fourth location. Then, the first optics system can begin measuring at the second position while the second optics mount moves to the fifth position.

Fiber Optical System

Figure 7:
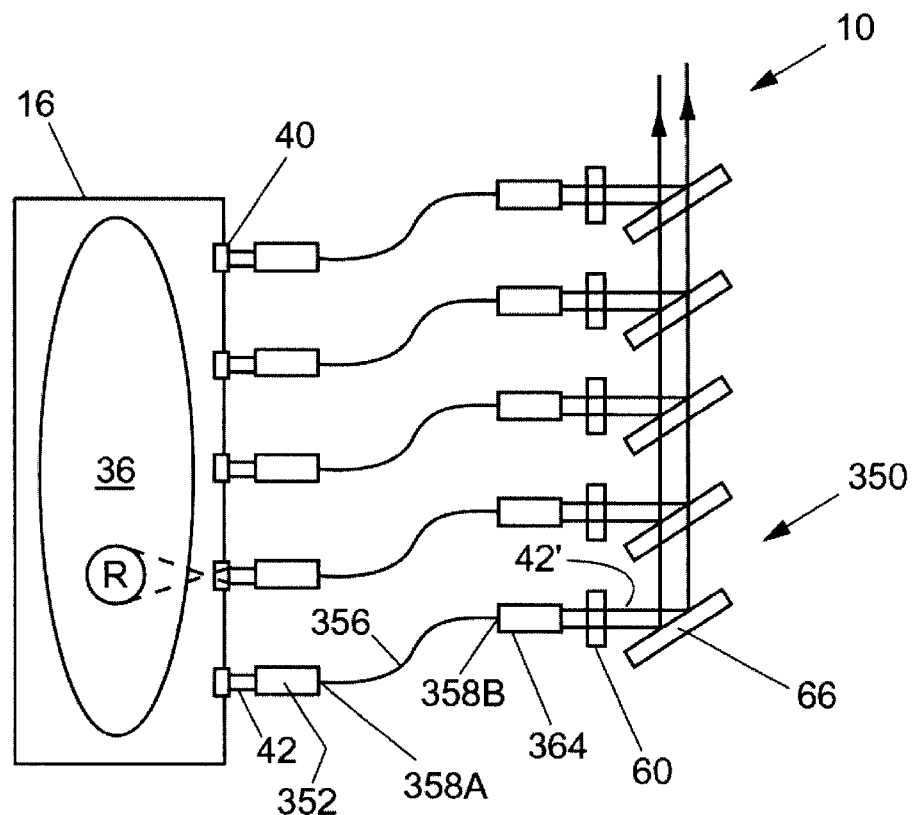
FIG. 7 is a schematic optical diagram of a third alternate embodiment of the apparatus of FIG. 1 that employs an optical fiber as part of the optical system for collecting and receiving light from the plasma.

With reference now to FIG. 7, there is shown a third alternate embodiment of apparatus 10 that replaces optical systems 50 with fiber optical systems 350 each comprising collection optics 352, an optical fiber 356 optically connected to the collection optics at a first fiber end 358a, and receiving optics 364 optically connected to the optical fiber at a second fiber end 358b. Shutters 60 and fold mirrors, as described above in connection with FIG. 1, are arranged adjacent receiving optics 364. Optical fiber 356 may be, for example, a single strand of single or multi-mode optical fiber, such as Part Number C309002BST available from Perkin-Elmer, Inc. Optical fiber 356 may also be an optical fiber bundle.

In operation, collection optics collect light 42 emanating from plasma 36 and passing through window 40, and couple the collected light into optical fiber end 358a. The light travels down the length of optical fiber 356 and is output at optical fiber end 358b. Optical fiber 356 may have a length on the order of meters or tens of meters so that shutters 60 and/or mirrors 66 can be located remote from plasma duct 16.

Figure 8:
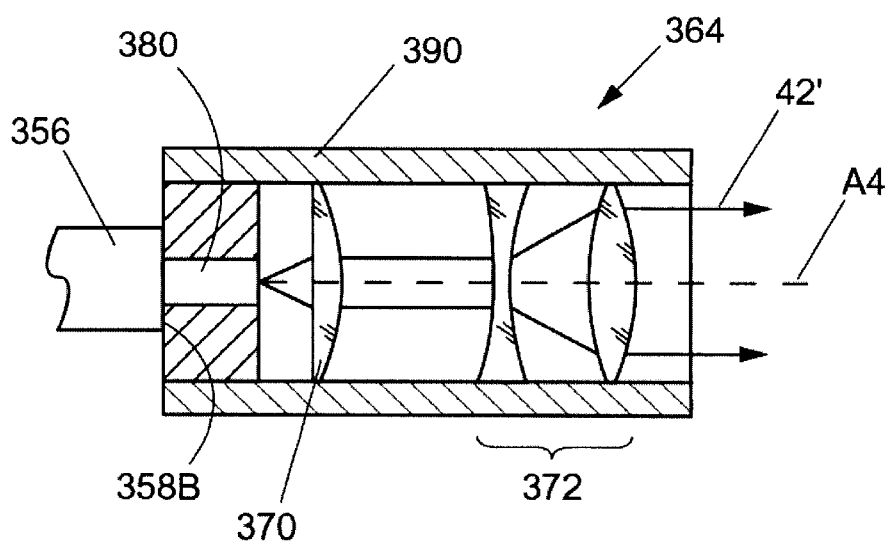
FIG. 8 is a close-up cross-sectional schematic diagram of an exemplary receiving optics for the apparatus of FIG. 7 that can also be used in reverse as the collection optics.

FIG. 8 depicts an exemplary optical arrangement for receiving optics 364. Collection optics 352 can utilize the same arrangement in reverse. Receiving optics 364 include, along an optical axis A4, a collimating (or focusing) lens 370 and a beam expander (or contractor) 372 arranged to receive from (or couple light to) core 380 of fiber 356. Receiving optics 364 includes a housing 390 that houses lenses 370 and 372 and that also holds fiber 356 to ensure proper coupling of light to (and from) the fiber. Lenses 370 and 372 are preferably axially adjustable to alter the degree of beam expansion and/or collimation. The geometry of collection optics 352 serves to define the region R in plasma 36 from which light is analyzed. The use of beam expanding or contracting optics allows the size of region R to be altered.

The method of operating this third alternate embodiment of apparatus 10 is the same as that described in flow diagram 200 of FIG. 2.

Divided Fiber Optical System

Figure 9:
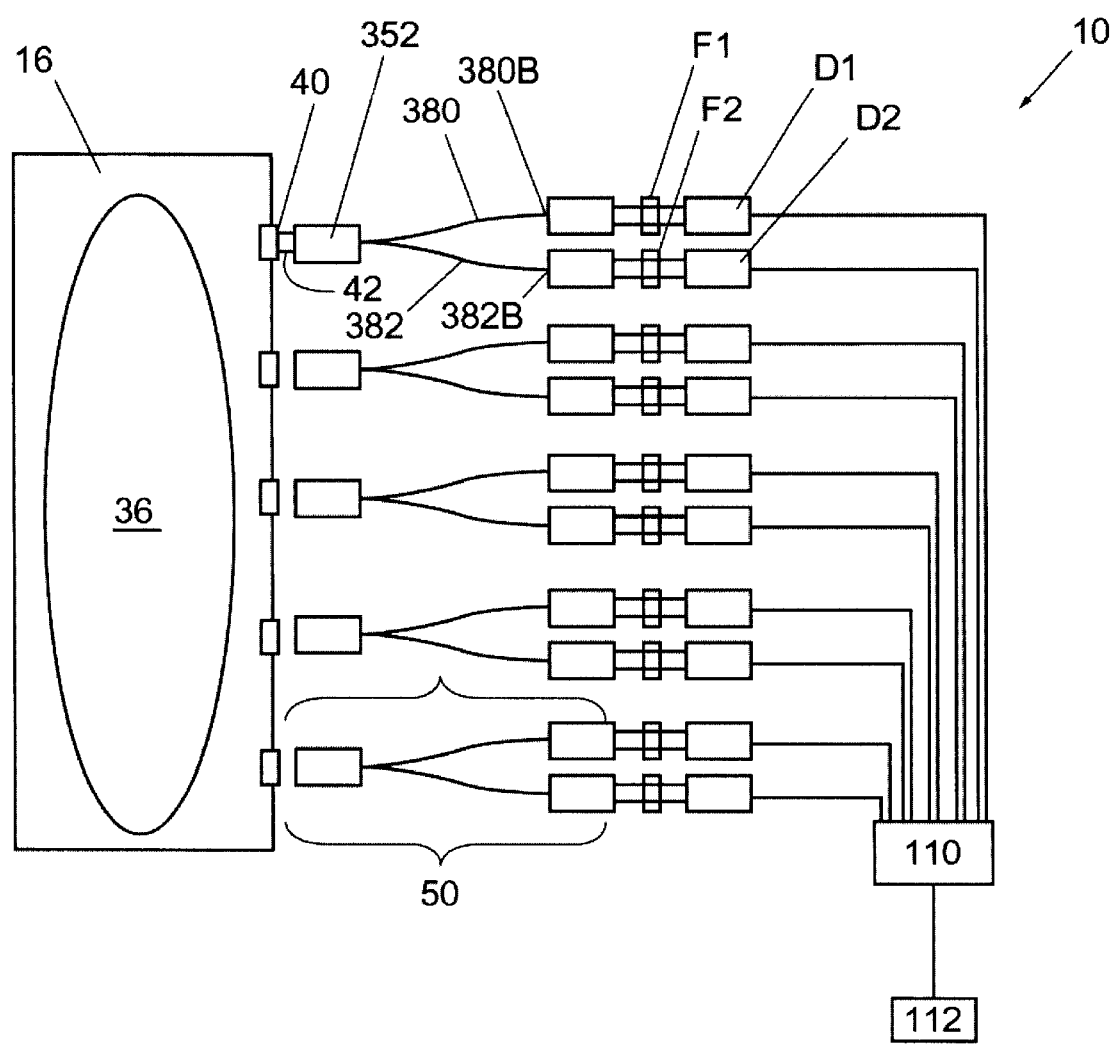
FIG. 9 is a schematic optical diagram of a fourth alternate embodiment of the apparatus of FIG. 1 that is similar to that of FIG. 7, but that employs a bifurcated or otherwise divided optical fiber or fiber bundle and respective detectors for each divided fiber.

With reference now to FIG. 9, in a fourth alternate embodiment of apparatus 10, optical fiber 356 is divided (e.g., bifurcated, trifurcated, etc.) into multiple fiber segments 380 and 382 having respective output ends 380b and 382b. Two segments are shown for the sake of illustration; more are possible. Segments 380 and 382 serve to split the light incident input end 358a of the optical fiber to form two light sources at the respective output ends. Light emanating from output ends 380b and 382b are received by two receiving optics 364a and 364b (each identical to receiving optics 364, described above) and coupled respectively to filters F1 and F2, and associated detectors D1 and D2. In the present fourth alternate embodiment, optical fiber 356 may be a fiber bundle that is divided into individual or sub-groups of fibers optically coupled to different detectors at their respective output ends. Note that where multiple detectors are used that correspond to each optical system 50, apparatus 10 does not require shutters. Rather, the voltage signals can be directly input in controller 110 and processed.

Translatable Fiber Optical System

Figure 10A:
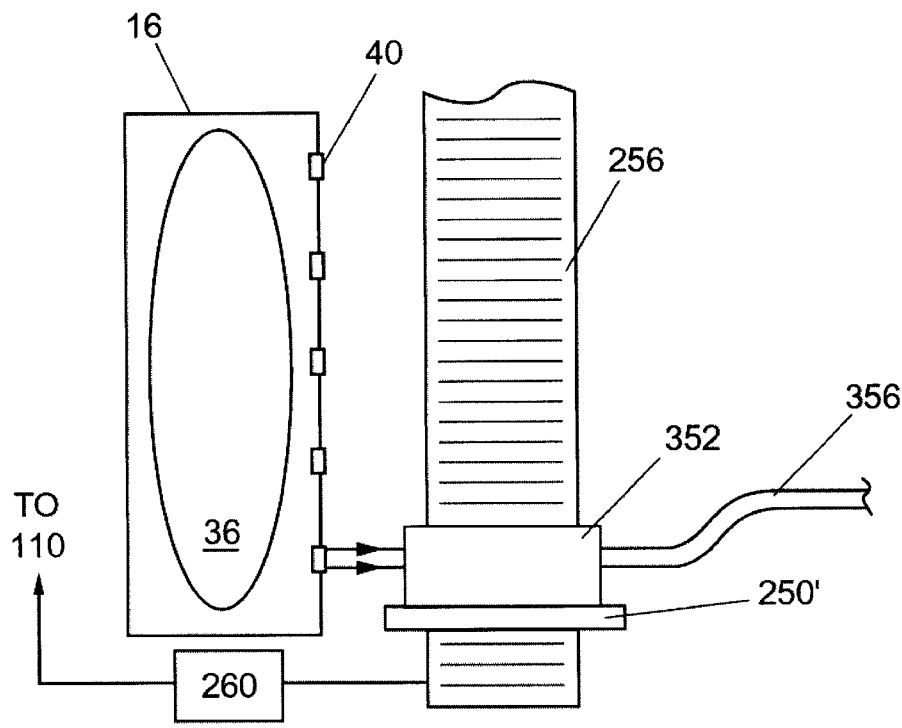
FIG. 10A is a schematic optical diagram of a fifth alternate embodiment of the apparatus of FIG. 1 similar to that of FIG. 9 and FIG. 5, employing the use of a translatable optics mount to which the collection optics is mounted.

With reference now also to FIG. 10A, in a fifth alternate embodiment of apparatus 10, collection optics 352 can be mounted to a small optics mount 250', which is in turn mechanically engaged with linear track 256 controlled by linear motor 260, in the manner described above in connection with FIG. 5 and the second alternate embodiment. The operation of apparatus 10 in this case is the same as that described above in connection with flow diagram 300 of FIG. 6. As with the second alternate embodiment of the translatable optical system described above in connection with FIG. 5, this fifth alternate embodiment also only requires one shutter and fold mirror.

Figure 10B:
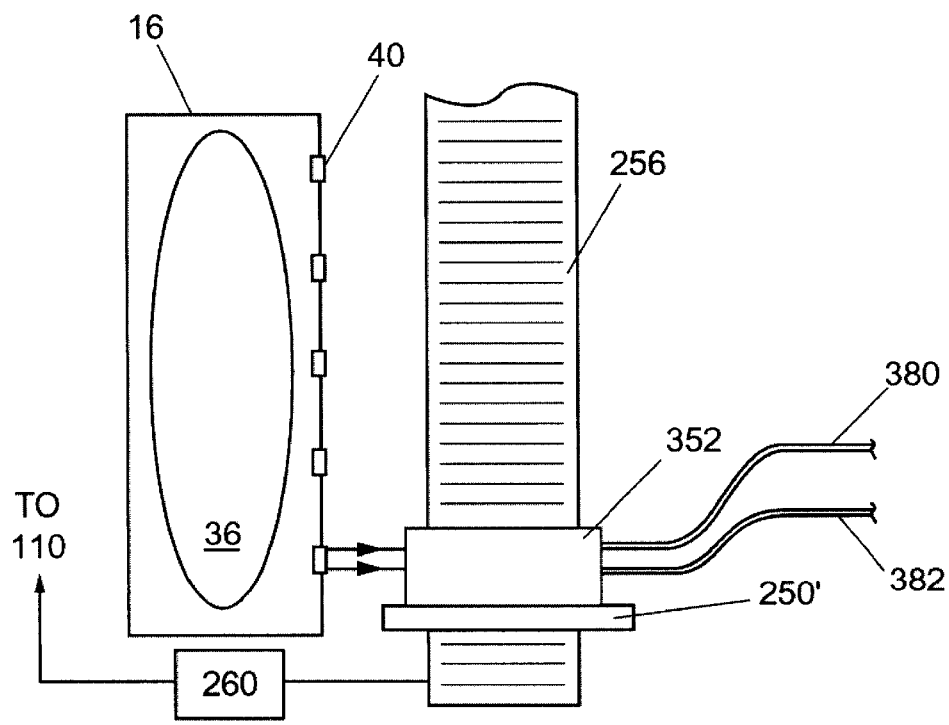
FIG. 10B is similar to FIG. 10A, but where the optical system includes a divided fiber.

Similarly, with reference to FIG. 10B, the same arrangement as described immediately above in connection with FIG. 10A and the single-fiber embodiment can be utilized to translate the divided fiber embodiment described above as the fourth alternate embodiment of the present invention.

Spectrometer Embodiment

Figure 11:
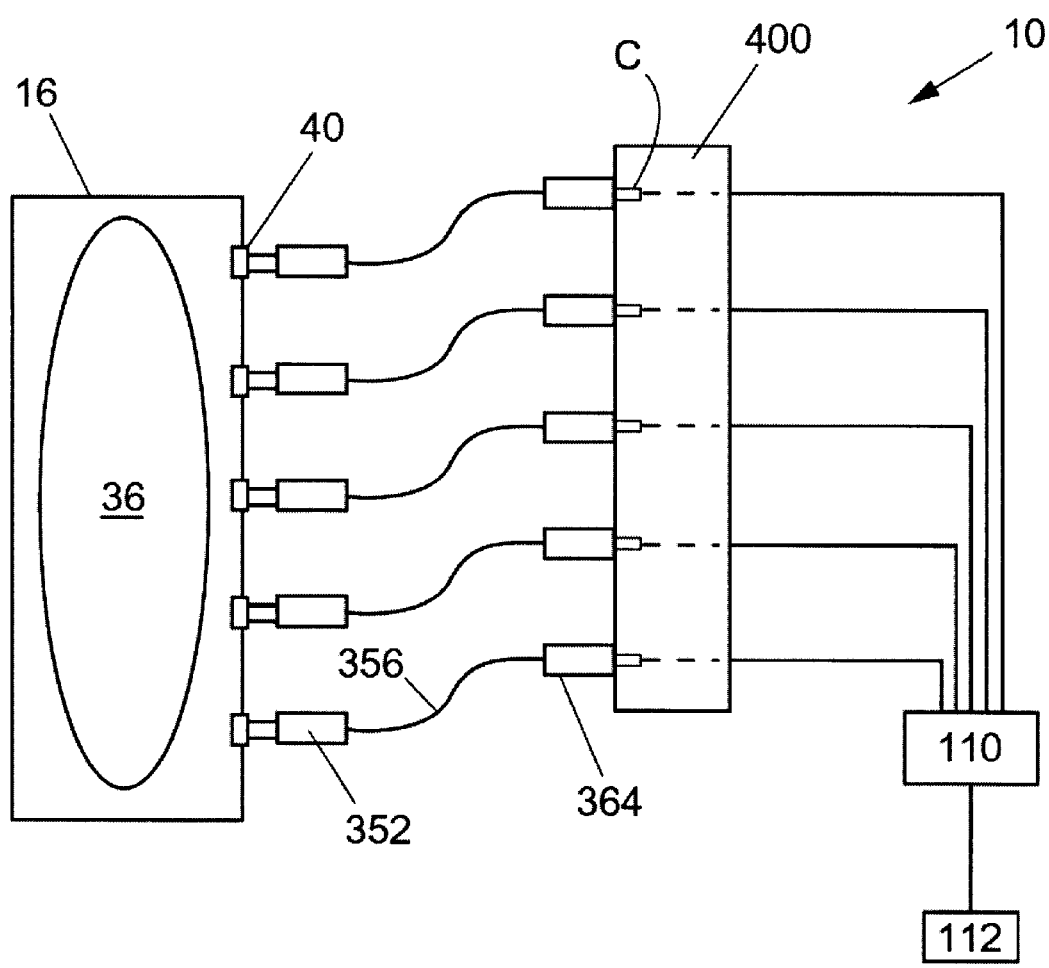
FIG. 11 is a schematic optical diagram of a sixth alternate embodiment of the apparatus of FIG. 1 similar to FIG. 7, wherein a multi-channel spectrometer replaces the filters and detectors of the apparatus of FIG. 7.

With reference now to FIG. 11, a sixth alternate embodiment of apparatus 10 is similar to that described above in connection with FIG. 7 and the third alternate embodiment of apparatus 10, except that in the present embodiment the output of receiving optics 364 is directly connected to the respective channel inputs C of a multi-channel spectrometer 400. Multi-channel spectrometers are commercially available, and an exemplary spectrometer system is the multi-channel (8) spectroscopy configuration with Model S2000-UV-VIS (grating no. 2) spectrometers, available from Ocean Optics, 5190 Golden Foothill Pkwy, El Dorado Hills, Calif. 95762. Spectrometer 400 is electrically connected to controller 110, which processes and displays the output from the spectrometer.

Method of Controlling the Plasma

With reference again to FIG. 1, controller 110 is electrically connected to electrical power source 38, which is electrically connected to electrodes E. Electrical power source 38 can be activated to selectively alter plasma 36 in response to the spectral analysis performed by controller 110.

Thus, with reference again to flow diagram 200 of FIG. 2 and flow diagram 300 of FIG. 6, the method of the present invention includes step 208 of selectively activating electrodes E to adjust plasma 36 based on the analysis performed in step 207.

For example, a first embodiment for use of the plasma duct 16 includes a plasma source wherein a process gas enters the plasma duct 16 through the upper opening 26, interacts with heated electrons in plasma 36 and exits the plasma duct 16 at lower opening 28 with prescribed chemical properties suitable for material processing in a vacuum chamber located below the plasma duct. Each electrode E may be a single-turn inductive coil driven by a RF generator through an impedance match network. The RF power to each coil (or electrode B) may be adjusted according to a prescribed recipe or in situ in order to produce a desired chemistry at the plasma duct exit. For additional details, the single-turn inductively coupled plasma source is described in U.S. patent application 60/277,966, filed Mar. 23, 2001, the contents of which are incorporated herein by reference. In oxide ($SiO_2$) etch, it is generally essential to produce a "low dissociation" plasma, i.e. one which has a minimal fluorine F radical concentration (or minimal F/Ar ratio). Alternatively, it is important to achieve high CFX to F ratios in order to achieve highly selective etch rates (i.e. the process environment achieves high oxide etch rates relative to photoresist and silicon etch rates). Therefore, as described above, the ratio of a first specie concentration (e.g. F) to a second species concentration (e.g. Ar) may be monitored along the length of the plasma duct 16, and the RF power to the electrodes E may be altered to affect a minimal F/Ar concentration ratio. Conversely, in poly-silicon etching, the specie concentration ratio, F/Ar, maybe maximized.

In a second embodiment, the plasma duct 16 may be a plasma pumping duct utilized to transport material from a first volume in connection with the first opening 26 of the plasma duct 16 to a second volume in connection with the second opening 28 of plasma duct 16. (For further details, a plasma vacuum pump of this nature is described in PCT/US99/12827 and U.S. Provisional applications serial Nos. 60/091,041, and 60/196,920. Those applications are incorporated herein by reference in their entirety.) Herein, the electrodes E may be either DC or RF biased, and they may be tuned to maximize the penetration of the plasma into plasma duct 16.

In a third embodiment, the plasma duct 16 may be a plasma abatement duct utilized to convert effluent material (such as perfluorocompounds) from a first volume in connection with the first opening 26 of the plasma duct 16 to either environmentally benign or gases suitable for a scrubbing system in a second volume in connection with the second opening 28 of plasma duct 16. Similarly, the electrodes E may be inductive coil whose input RF power is adjusted to either minimize specific specie concentrations (e.g. PFCs) or maximize the production of pre-specified reaction products (e.g. $CO_2$, etc.).

With reference again to FIG. 1, electrodes E may be a single RF electrode that extends circumferentially around duct 16. RF power at suitable frequencies and power levels is applied to this electrode through conventional matching networks (not shown). Faraday shields (not shown) may also be used, as is well known to those skilled in the art of RF plasma sources. The purpose of the ISP source is to offset the loss of plasma and heat to the walls of the conduit by leakage through the ring cusps. Through suitable adjustment of the RF power to the electrode 140 the plasma density and temperature can be maintained uniform throughout the length of the duct.

Apparatus Calibration

Spectral (wavelength) calibration of the spectral emissions recorded using any one of the above-described embodiments of apparatus 10 can be accomplished by replacing the plasma "light source" with a light source having a known spectrum, such as commercially available spectral calibration lamp. Such lamps are available through Oriel Instruments, Inc. For example, Oriel Instruments offers the following lamp types: Hg(Ar)-(Model #6035), Hg(Ne)-(6034), Xenon-(6033), Argon-(6030), Neon-(6032) and Krypton-(6031); each of which offers a different range of wavelengths extending between the ultraviolet (UV) and infrared (IR) spectrums. As an option, the calibration lamps may be fiber optically coupled to provide light over the entire UV to IR spectrum from a single output.

Although some embodiment described herein use plural windows, along a length of the duct, in an alternate embodiment, a single window runs the length of the portion of the duct to be examined, and the characteristics of the plasma are simply monitored at multiple locations along the window. In fact, as would be appreciated by one of ordinary skill in the art from this specification, the optical system need not receive light through every window, or conversely may include greater than one optical component per window (e.g., greater than one set of collection optics, beam splitters and filters per window).

The many features and advantages of the present invention are apparent from the detailed specification, and, thus, it is intended by the appended claims to cover all such features and advantages of the described apparatus that follow the true spirit and scope of the invention. Furthermore, since numerous modifications and changes will readily occur to those of skill in the art, it is not desired to limit the invention to the exact construction and operation described herein. Accordingly, other embodiments are within the scope of the appended claims.

What is claimed is:

1. An apparatus for detecting the spectra of light emitted by a plasma at plural locations along the plasma, comprising:
    a) an optical system;
    b) an optics mount, coupled to said optical system, for positioning said optical system to receive light emitted from the plural locations;
    c) a beam splitter arranged so as to receive light from said optical system and direct the light along first and second optical paths;
    d) first and second detectors respectively arranged downstream of said beam splitter to convert the light along said first and second optical paths into respective first and second electrical signals representative of the intensity of light incident said first and second detectors, wherein the first and second detectors detect different wavelength ranges of the light; and
    e) a controller configured to process said electrical signals to determine a property of said plasma at each of said plural locations.

2. An apparatus according to claim 1, wherein said controller is electrically connected to said first and second detectors for receiving and processing said electrical signals so as to provide information pertaining to the spectral content of the light incident said first and second detectors.

3. An apparatus according to claim 1, further comprising at least one filter interposed between the beam splitter and at least one of the first and second detectors.

4. An apparatus for detecting the spectra of light emitted by a plasma at plural locations along the plasma, comprising:
    a) plural optical systems arranged to receive light from the plural locations along the plasma;
    b) a beam splitter arranged relative to said optical systems so as to receive light from said optical systems and direct the light along first and second optical paths; and
    c) first and second detectors respectively arranged downstream of said beam splitter so as to convert said light along the first and second optical paths into respective first and second electrical signals representative of the intensity of light incident said first and second detectors, wherein the first and second detectors detect different wavelength ranges of the light; and
    d) a controller configured to process said electrical signals to determine a property of said plasma at each of said plural locations.

5. An apparatus according to claim 4, further comprising an electrical power source electrically connected to at least one electrode in operative communication with the plasma.

6. An apparatus according to claim 4, wherein said optical system comprises at least one of a Galilean telescope and an inverse Galilean telescope.

7. An apparatus according to claim 4, wherein each said optical system comprises:
    a) collection optics arranged to collect light emanating from a corresponding one of the plural locations;
    b) an optical fiber having an input end optically coupled to said collection optics and an output end; and
    c) receiving optics optically coupled to said optical fiber output end.

8. An apparatus according to claim 4, wherein each optical system includes a fold mirror for directing light exiting the optical system.

9. An apparatus according to claim 4, wherein said first and second electrical signals are voltages.

10. An apparatus for detecting the optical emission spectra at plural locations along a plasma, comprising:
    a) plural optical systems arranged to receive light from the plural locations along the plasma;
    b) a multiple-filter device having a plurality of optical filters, each optical filter having a different bandwidth and adapted to selectively insert one of said plurality of optical filters into said optical path; and c) a detector arranged downstream of said multiple-filter device so as to detect light passing through said one of said plurality of optical filters inserted into said optical path and convert said light into an electrical signal representative of the intensity of light incident said detector; and d) a controller configured to process said electrical signals to determine a property of said plasma at each of said plural locations.

11. An apparatus according to claim 10, wherein said a controller is electrically connected to said detector and to said multiple-filter device for controlling the insertion of one of said optical filters into said optical path and coordinating the receiving and processing electrical signals from said detector so as to provide data pertaining to the spectral content of the light incident said detector through said optical filters.

12. An apparatus according to claim 11, wherein each of said optical systems includes an electronic shutter electrically connected to and controlled by said controller via electronic signals.

13. An apparatus according to claim 10, wherein each of said optical systems includes a fold mirror for redirecting light exiting the optical system.

14. An apparatus according to claim 10, wherein said electrical signal is a voltage.

15. An apparatus for detecting an optical emission spectra at plural locations along a plasma, comprising:

a) a collection optical system arranged to collect light from the plural locations and transmit the collected light from a first end of an optical fiber to at least two second ends of the optical fiber;

b) at least two detectors arranged to convert light emanating from the at least two second ends into electrical signals, wherein each of the at least two detectors detects a different wavelength of light; and c) a controller configured to process said electrical signals to determine a property of said plasma at each of said plural locations.

16. An apparatus according to claim 15, wherein said a controller is electrically connected to said at least two detectors for receiving and processing said electrical signals therefrom so as to provide information pertaining to a spectral content of the light incident said at least two detectors.

17. An apparatus according to claim 15, wherein the at least two detectors comprise a multi-channel spectrometer for generating electrical signals representative of the spectral content of the light from the plural locations.

18. A method of measuring the spectral properties of light emitted by a plasma at different regions of the plasma, comprising the steps of:

a) sequentially collecting light generated by plural regions of the plasma;

b) detecting the light using a detector capable of detecting light in at least two wavelength ranges; and c) generating, with the detector, electrical signals representative of the intensity of the light detected in each of the at least two wavelength ranges for the plural regions of the plasma; and d) processing the electrical signals to determine a property of the plasma at each of said different regions.

19. A method according to claim 18, wherein said step b) includes passing the light through at least one of (1) plural filters and (2) a multiple-filter device.

20. A method of measuring the spectral properties of light emitted from plural locations in a plasma, comprising the steps of:

a) directing first and second light beams emanating from respective first and second locations of the multiple locations through first and second optical systems, respectively; and b) generating first and second electrical signals, corresponding to first and second wavelength ranges, with first and second detectors, respectively; and c) processing the electrical signals to determine a property of the plasma at each of said different regions.

21. A method according to claim 20, further comprising the step of comparing said first and second electrical signals.

22. A method according to claim 20, wherein the first and second optical systems each comprise a shutter such that (1) light is not passed to the first detector when light is passed from the second detector and (2) light is not passed to the second detector when light is passed from the first detector.

23. A method according to claim 20, further comprising the step of altering the plasma properties based on the first and second electrical signals.

24. A method of measuring the spectral properties of light emitted by a plasma at different regions of the plasma, comprising the steps of:

a) sequentially collecting light generated by the plasma at plural regions of the different regions;

b) separating the sequentially collected light into at least two paths;

c) detecting the light from each path using corresponding detectors, each detector corresponding to a different wavelength range; and d) generating, with each detector, a corresponding electrical signal representative of the intensity of the light detected; and e) processing the electrical signals to determine a property of the plasma at each of said different regions.

25. A method according to claim 24, wherein step a) comprises the step of sequentially receiving light from only one region at a time.

26. A method according to claim 24, wherein said step a) comprises providing an optical system adjacent each region so as to be in optical communication with said each region.

27. A method according to claim 24, wherein said step a) includes sequentially positioning a single optical system to be in optical communication with different regions of said plasma sequentially.

28. A method according to claim 24, wherein said step a) comprises passing the collected light through an optical fiber.

29. A method according to claim 24, wherein said step b) comprises passing the collected light through at least two optical fibers each having an output end optically coupled to a respective one of the detectors.

30. A method according to claim 24, further comprising the step of selectively providing electrical power to at least one electrode, based on the electrical signals.

31. A method of measuring the spectral properties of light emitted by a plasma at different regions of the plasma, comprising the steps of:

a) collecting light generated by the plasma in plural different regions;

b) passing the collected light to corresponding input channels in a multi-channel spectrometer; and c) generating corresponding electrical signals representative of the spectrum of light detected for each input channel; and d) processing the electrical signals to determine a property of the plasma at each of said different regions.

32. A method according to claim 31, wherein said step b) comprises the step of sequentially blocking light from being transmitted through all but one of the input channels.

33. A method according to claim 31, wherein said step a) includes providing an optical system adjacent at least one window so as to be in optical communication with said plasma.

34. A method according to claim 31, wherein said step a) includes sequentially positioning a single optical system adjacent at least one window so as to be in optical communication with said plasma.

35. A method according to claim 31, wherein said step a) includes passing the collected light through an optical fiber.

36. A method according to claim 31, further comprising the step of selectively providing electrical power to at least one electrode, based on said electrical signals.

37. A method of determining a plasma property comprising:

(a) collecting light generated by a first region of the plasma;

(b) collecting light generated by a second region of the plasma; and (c) analyzing optical properties of the light collected from each of the first and second regions to determine a plasma property at each of the first and second regions.

38. An apparatus for determining a plasma property comprising:

(a) means for collecting light generated by a first region of the plasma;

(b) means for collecting light generated by a second region of the plasma; and (c) means for analyzing optical properties of the light collected from each of the first and second regions to determine a plasma property at each of the first and second regions.

* * * * *